United States Patent
Koschmieder

(10) Patent No.: US 8,277,047 B2
(45) Date of Patent: Oct. 2, 2012

(54) ILLUMINATION UNIT FOR THE GENERATION OF OPTICAL SECTIONAL IMAGES IN TRANSPARENT MEDIA, IN PARTICULAR IN THE EYE

(75) Inventor: Ingo Koschmieder, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1144 days.

(21) Appl. No.: 10/473,460

(22) PCT Filed: Nov. 11, 2002

(86) PCT No.: PCT/EP02/12561
§ 371 (c)(1),
(2), (4) Date: Sep. 26, 2003

(87) PCT Pub. No.: WO03/041573
PCT Pub. Date: May 22, 2003

(65) Prior Publication Data
US 2004/0116811 A1    Jun. 17, 2004

(30) Foreign Application Priority Data

Nov. 12, 2001   (DE) .................... 101 55 464

(51) Int. Cl.
*A61B 3/10* (2006.01)

(52) U.S. Cl. .......................... 351/214; 351/206; 600/476
(58) Field of Classification Search .................. 351/214, 351/206, 219, 211, 221; 600/407–410, 476–480
See application file for complete search history.

(56) References Cited

U.S. PATENT DOCUMENTS
4,213,678 A    7/1980    Pomerantzeff et al.
(Continued)

FOREIGN PATENT DOCUMENTS
DE    198 12 050    9/1999
(Continued)

OTHER PUBLICATIONS
"Ophthalmologic-optical instruments", 1987, Ferdinand Enke Verlag Stuttgart, pp. 99ff and 137ff, Rassow, B. et al.

*Primary Examiner* — Sanjay Cattungal
(74) *Attorney, Agent, or Firm* — Frommer Lawrence & Haug LLP

(57) ABSTRACT

Illumination unit for the generation of optical sectional images in transparent media, particularly in the eye is disclosed. In the arrangement according to the invention, the low-divergence beams emitted by a laser serving as illumination source are imaged on or in the eye under examination by a reflection element which is controllable in a defined manner and beam deflection elements present in the beam path. The optical sectional images resulting in and on the eye can be observed and/or recorded, further processed and evaluated with an image processing unit in a known manner. In the solution according to the invention, a sectional image is generated by the deliberate periodic beam deflection of a particularly fine laser beam with high depth of focus, which sectional image remains sharp through the entire dimension of the object to be examined and makes possible an improved evaluation. The intensity of the laser beam bundle can be varied in such a way that it is sufficient for observation and documentation, but so that the diameter of the beam bundle is fine enough for a high detail resolution.

5 Claims, 2 Drawing Sheets

U.S. PATENT DOCUMENTS

| | | | |
|---|---|---|---|
| 4,541,697 A * | 9/1985 | Remijan | 351/211 |
| 4,877,321 A * | 10/1989 | Ichihashi et al. | 351/214 |
| 5,139,022 A | 8/1992 | Lempert | |
| 5,404,884 A | 4/1995 | Lempert | |
| 5,430,509 A * | 7/1995 | Kobayashi | 351/221 |
| 5,781,324 A * | 7/1998 | Nishina | 359/206.1 |
| 5,784,146 A | 7/1998 | Nanjo et al. | |
| 6,149,643 A * | 11/2000 | Herekar et al. | 606/5 |
| 6,275,718 B1 | 8/2001 | Lempert | |
| 6,276,798 B1 * | 8/2001 | Gil et al. | 351/206 |
| 6,523,955 B1 * | 2/2003 | Eberl et al. | 351/211 |
| 6,561,648 B2 * | 5/2003 | Thomas | 351/221 |
| 6,594,090 B2 * | 7/2003 | Kruschwitz et al. | 359/707 |
| 6,609,794 B2 * | 8/2003 | Levine | 351/221 |
| 6,836,337 B2 * | 12/2004 | Cornsweet | 356/517 |
| 7,561,185 B2 * | 7/2009 | Yamasaki et al. | 348/208.99 |
| 2003/0007125 A1 * | 1/2003 | Levine | 351/206 |
| 2003/0039036 A1 * | 2/2003 | Kruschwitz et al. | 359/707 |
| 2004/0125361 A1 * | 7/2004 | Riza et al. | 356/121 |
| 2005/0070772 A1 * | 3/2005 | Cornsweet | 600/319 |

FOREIGN PATENT DOCUMENTS

| | | |
|---|---|---|
| EP | 0 380 197 | 8/1990 |
| JP | 01-285242 | 11/1989 |

\* cited by examiner

ILLUMINATION UNIT FOR THE GENERATION OF OPTICAL SECTIONAL IMAGES IN TRANSPARENT MEDIA, IN PARTICULAR IN THE EYE

CROSS-REFERENCE TO RELATED APPLICATIONS

This application claims priority of PCT Application Serial No. PCT/EP02/12561, filed Nov. 11, 2002 and German Application No. 101 55 464.8, filed Nov. 12, 2001, the complete disclosures of which are hereby incorporated by reference.

BACKGROUND OF THE INVENTION a) Field of the Invention

The present invention is directed to a special illumination unit for generating a variable slit image such as is used in ophthalmological examination instruments, including slit lamps. A light section is generated by slit image projection in the more or less transparent object under examination, e.g., in the interior of the eye. The parameters of the section bundle are variable, particularly the angle of incidence, the dimensions of the slit image, its intensity and the spectral composition. Information about the object under examination can be acquired from the shape, position and intensity of the scattered light of the sectional image generated in this way.

b) Description of the Related Art

In slit lamps such as those described in Rassow, B. et al., "Ophthalmologic-optical instruments", 1987, Ferdinand Enke Verlag Stuttgart, pages 99ff and 137ff, mechanical/optical elements such as slit diaphragms have been used up until now to generate slit imaging. The variable, smallest possible slit widths which are required for high optical detail resolution within the optical section are very difficult to achieve. Further, the mechanical component groups are very cumbersome to adjust, and this is made even more difficult by the thermal expansion of the component groups, among other things. Reproducibility of adjustments for measurement purposes is possible only to a limited extent. The multiplicity of possible illuminated field geometries is extremely limited by the fixed slit diaphragms and pinhole diaphragms and the space required by the latter.

Since slit image projection involves optical imaging with a physically defined depth of focus, the imaging must always be focused strictly on the point of examination. A section bundle which is focused over the entire extension of the human eye can not be achieved with the solutions mentioned above. While conditions can be improved with an arrangement based on the Scheimpflug principle, the technical expenditure is correspondingly greater.

DE 198 12 050 A1 describes a method and an arrangement for illumination in an ocular microscope. A wide variety of illuminating mark geometries is generated by means of optoelectronic components. The illuminated field geometries are projected on the anterior portion and fundus of the eye and are used for general examination of the eye.

Methods and arrangements for illuminating the anterior segments of the eye in which a planar configured laser is used as light source are described in U.S. Pat. Nos. 5,404,884, 5,139,022 and 6,275,718. However, in these solutions the limited variability of the slit dimensions, the utilized wavelength of the laser sources, and the lack of a possibility for generating multiple-slit projections are disadvantageous under certain circumstances. The described arrangements are not slit lamp devices used in normal diagnostic operation.

Further, the system for receiving the scattered light from the eye has a physically limited depth of focus which can not completely acquire the expansion area of the sharp sectional laser image.

OBJECT AND SUMMARY OF THE INVENTION

It is the primary object of the present invention to further develop the known solutions in such a way that a sufficient light intensity for observation and documentation, particularly with analog or digital image acquisition technology, can be ensured in spite of the smallest possible slit width and greatest possible depth of focus which are required for high optical detail resolution within the optical section.

According to the invention, this object is met by an illumination for generating optical sectional images in transparent media, particularly in the eye, comprising a laser which is provided as illumination source and a reflection element which is controllable in a defined manner for the deliberate deflection of the laser beams.

With the proposed solution for an illumination unit for generating optical sectional images in the eye, a sectional image is generated by the deliberate periodic beam deflection of a particularly fine laser beam with high depth of focus, which sectional image remains sharp through the entire dimension of the object to be examined and makes possible an improved evaluation. The intensity of the laser beam bundle can be varied in such a way that it is sufficient for observation and documentation, but so that the diameter of the beam bundle is fine enough for a high detail resolution. The proposed illumination unit could be constructed in such a way that it is used in addition to an existing illumination unit of an ophthalmological instrument such as a slit lamp. As an add-on module for existing ophthalmological instruments, it could substantially simplify examinations of the human eye through broad application and improve the accuracy of the examination results.

The invention will be described in more detail in the following with reference to an embodiment example.

DESCRIPTION OF THE PREFERRED EMBODIMENTS

Figure 1:
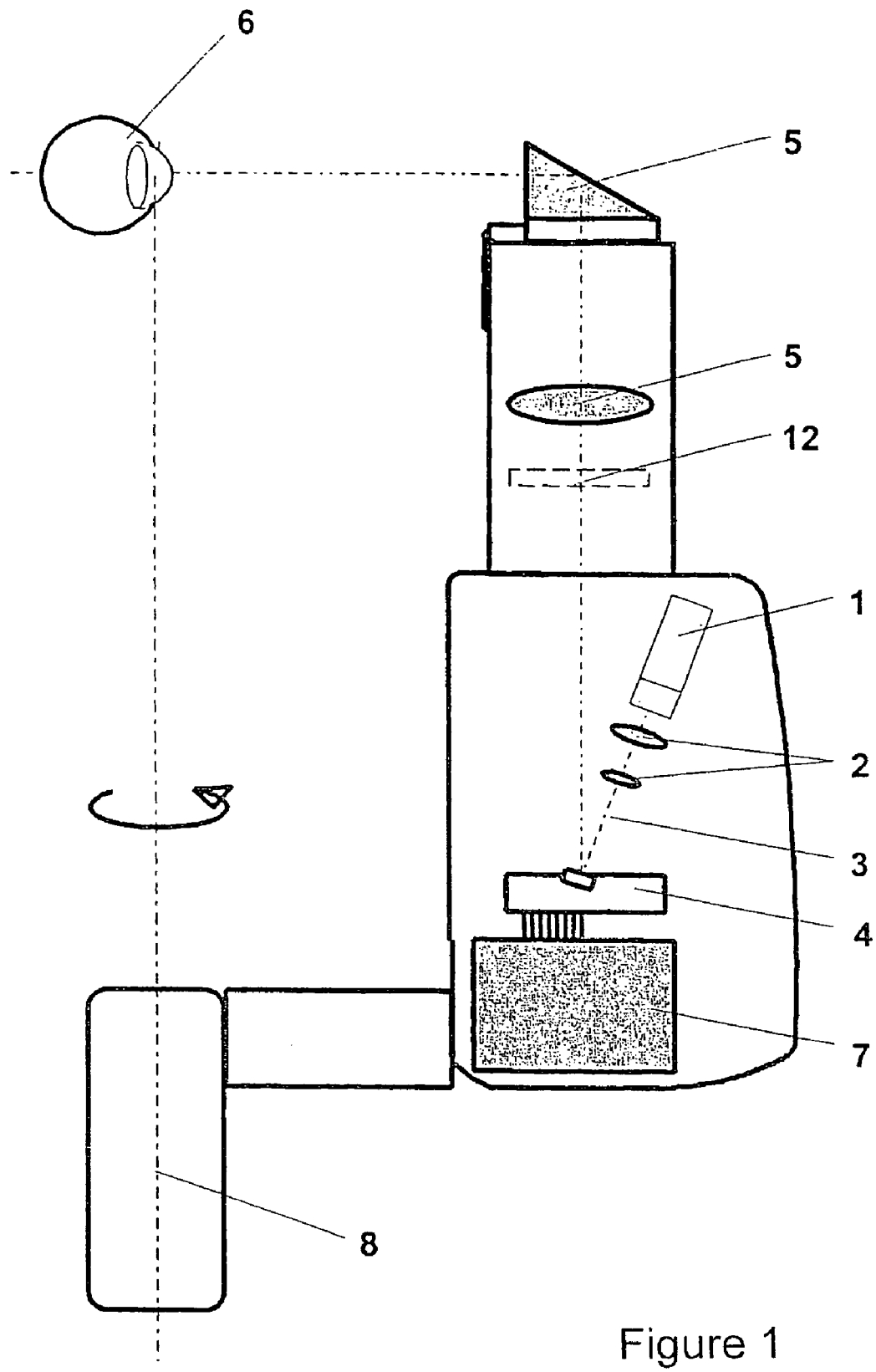
FIG. 1 is a schematic view of a slit lamp with the illumination unit according to the invention.

FIG. 1 shows the construction of a slit lamp with the illumination unit, according to the invention, for generating optical sectional images. The low-divergence beams proceeding from the laser serving as illumination source 1 are imaged on or in the eye 6 under examination by a reflection element 4 which is controllable in a defined manner and beam-shaping and beam-deflection elements (shown schematically) in the beam path. The angle and the direction of the laser beam 3 directed onto the eye under examination are freely selectable.

A laser diode module, for example, is used as illumination source, preferably in the blue or green spectral range. Illumination with light in the green or blue spectral range results in higher scattering in the transparent media of the eye, which leads to clearer sectional images for optical diagnosis. A very fine, low-divergence laser beam 3 is generated by means of focusing optics 2. This laser beam 3 impinges at a determined angle and distance on the reflection element 4 whose frequency and amplitude can be controlled by the control unit 7. The reflection element 4 is a mirror which has small dimensions and which is tiltable in two or more directions independent from one another. This so-called microscanner mirror chip preferably belongs to the group of MEMS (microelectromechanical systems) and can be constructed in any manner desired. A chip of this type is available, for example, from Fraunhofer-Institut für Mikroelektronische Schaltungen und Systeme Dresden under the trade name "Resonanter 1D- und 2D-Mikroscannerspiegel".

Also, a DMD (digital mirror device) type microscanner mirror chip such as that available from Texas Instruments, for example, can be used as a reflection element.

Figure 2:
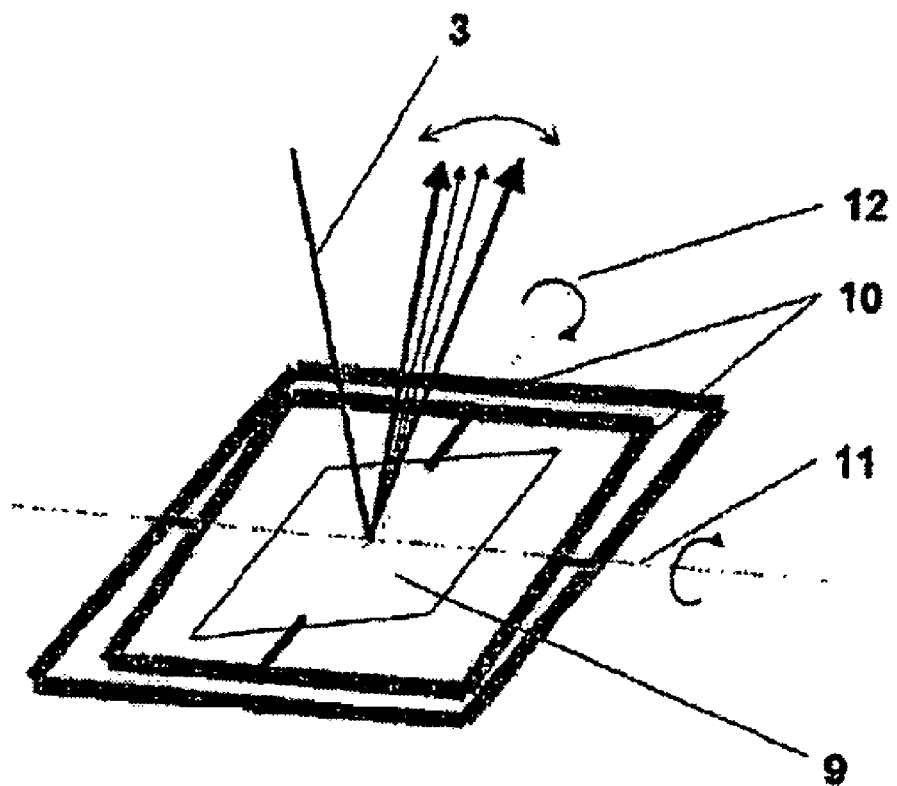
FIG. 2 is a schematic view of a microscanner mirror.

FIG. 2 shows a schematic view of a MEMS type microscanner mirror chip. The actual mirror element 9 is tiltable along axes 11 and 12 by means of the holder frame 10. Tilting around the respective axes 11 and 12 can be carried out, for example, by generating harmonic mechanical oscillations of suitable frequency and amplitude by means of electrostatic control. The microscanner mirror, which is fastened by torsion springs or by a universal joint suspension, is accordingly set in harmonic mechanical oscillations. In this way, many different shapes can be imaged on or in the eye under examination from the punctiform low-divergence laser beam 3. When the microscanner mirror oscillates in only one direction, for example, the image of a slit is generated.

In the microscanner mirror chip produced by Fraunhofer-Institut, the adjustable oscillation frequencies are between 150 Hz and 20 kHz depending on the image to be produced. The amplitude of the oscillation is directly proportional to the drive voltage in this microscanner mirror chip and can be regulated by means of this drive voltage. Deflecting angles of up to 60° can be achieved by the electrostatic drive principle.

In principle, electrostatic, thermomechanical, piezoelectric and magnetic excitation forms are possible for the control of the microscanner minors. A large number of displayable images, e.g., single slits and multiple slits, grids and rasters, result from the many possibilities of modulation with respect to frequency, amplitude and intensity.

A particular advantage of the illumination unit according to the invention consists in the possibility of a quasi-simultaneous imaging of a plurality of slit images on or in the eye under examination. In this way, the examination period can be shortened and the physical stress on the patient can be substantially reduced.

The laser beam 3 which can be changed in this way with respect to its propagation direction and also with respect to its intensity by additional modulation is deflected on or in the eye 6 under examination by the beam-shaping and beam-deflecting element 5.

The optical sectional images resulting in the eye 6 can be observed in the usual manner, e.g., with a variable-magnification stereo microscope or similar arrangement. Current ophthalmological instruments generally have, in addition to an observation system, an image processing unit by means of which the sectional images can be recorded, further processed and evaluated.

Because of its small dimensions, the illumination system according to the invention can be integrated in many different ophthalmological examination instruments, especially slit lamps. The illumination unit can be combined with the conventional, existing illumination arrangement or can be used separately. It is also possible to use the illumination unit as an add-on module for expanding existing ophthalmological instruments in order to substantially simplify examinations of the human eye and to improve the accuracy of the examination results. Modern ophthalmological examination instruments have additional documentation devices such as photo/video components for analog and digital image recording and image processing and an automatic image evaluation for obtaining measurement values of the object under examination. In order to increase the depth of focus during documentation, the recording unit with its receiver (e.g., CCD chip) can be inclined relative to the optical axis so as to be adapted to the angle of the slit input radiation direction corresponding to the Scheimpflug condition. The effect can be monitored with a monitor image in an advantageous manner.

In the illumination unit according to the invention, the intensity of the laser source can advantageously be selected in such a way that it is sufficient for observation and documentation, but such that the diameter of the beam bundle is fine enough for a high detail resolution and limiting values for the spectral irradiation strength on the fundus of the eye are not exceeded. Further advantageous effects, e.g., spatial separation of projection structures, can be achieved by means of a suitable modulation of the intensity of the light source. For this purpose, current laser diode modules generally have an additional connection for applying a modulation signal. Different illumination structures such as point grids and line grids or multiple-slit images can be realized in this way. These illumination structures can likewise be generated as dynamic processes in order to automate certain sequences or processes.

The described illumination unit serves to generate optical sectional images not only in the eye but also in different transparent media. The illumination unit can also be used, for example, for examination of liquid layers and/or for testing optical components such as lenses, prisms, and so on. It can be advantageous that the microscanner mirror is not set in oscillations but rather executes a slow scanning movement over the object to be tested. Since not all microscanner mirrors offer the possibility for a control of this kind, an appropriate model must be selected.

While the foregoing description and drawings represent the present invention, it will be obvious to those skilled in the art that various changes may be made therein without departing from the true spirit and scope of the present invention.

The invention claimed is:

1. An slit lamp comprising:
    a laser being provided as an illumination source; and
    one reflection element that, during use of the illumination unit, is controllable by a drive voltage in a defined manner for the deliberate deflection of the laser beam and is tiltable about two axes independent from one another;
    wherein the one reflection element is controlled such that an amplitude of an oscillation of the one reflection element is proportional to the drive voltage, and the deliberate deflection generates optical sectional images in transparent media; and
    wherein each of the two independent axes, about which the reflection element is tiltable, is arranged to always intersect both with an upstream beam path and with a downstream beam path of the laser beam which is deflected by the reflection element.

2. The slit lamp according to claim 1;
    wherein the beam emitted by the laser serving as illumination source has a low divergence; and/or
    wherein the beam emitted by the laser is in the blue or green spectral region; and/or
    wherein the intensity of the illumination unit is controllable; and/or
    wherein the illumination unit has beam-shaping elements.

3. The slit lamp according to claim 1;
wherein the illumination source is a laser diode module.

4. The slit lamp according to claim 1;
wherein an oscillation frequency and the amplitude of the oscillation of the reflection element are controllable;
wherein the reflection element is a mirror of small dimensions; and
wherein the reflection element is a microscanner mirror chip of any type of construction.

5. An ophthalmological examination instrument;
wherein it contains an slit lamp according to claim 1;
wherein the illumination unit is used in combination with a conventional illumination device and can be switched on when needed, or wherein the illumination unit is used separately from the conventional illumination device and can be added optionally;
wherein additional documentation devices are provided;
wherein there is an additional automatic image evaluation for obtaining measurement values of the object under examination; and
wherein the documentation device can be tilted at an angle for increasing the depth of focus according to the Scheimpflug condition so as to improve acquisition of the spatial extent of the sectional image through its entire dimension.

\* \* \* \* \*